US00PP28995P3

(12) United States Plant Patent
Brazelton et al.

(10) Patent No.: US PP28,995 P3
(45) Date of Patent: Feb. 27, 2018

(54) BLUEBERRY PLANT NAMED 'FF03-178'

(50) Latin Name: *Vaccinium corymbosum*
Varietal Denomination: FF03-178

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES); Paul Lyrene, Micanopy, FL (US)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 15/330,617

(22) Filed: Oct. 19, 2016

(65) Prior Publication Data

US 2017/0112032 P1 Apr. 20, 2017

Related U.S. Application Data

(60) Provisional application No. 62/285,130, filed on Oct. 19, 2015.

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — Hahn Loeser & Parks, LLP

(57) ABSTRACT

The new blueberry plant variety 'FF03-178' is provided. The variety is produced from a cross of 'FL00-62' and 'FL96-24', which can be distinguished by its outstanding features. 'FF03-178' is a commercial variety intended for the hand harvest fresh market. The variety is medium vigorous, medium branched and leafy and produces a high yield of large fruit.

5 Drawing Sheets

CROSS REFERENCE TO RELATED APPLICATIONS

This application claims the benefit of U.S. Provisional Patent Application No. 62/285,130 filed on Oct. 19, 2015, which is incorporated herein by reference in its entirety as though fully set forth.

Latin name of the family, genus, and species: Family—Ericaceae. Genus—*Vaccinium*. Species—*corymbosum* hybrid.

Variety denomination: The new blueberry plant claimed is of the variety denominated 'FF03-178'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry known as 'DivinaBlue' a *Vaccinium corymbosum* hybrid referred to as 'FF03-178' selection as herein described and illustrated.

SUMMARY OF THE INVENTION

The new blueberry selection 'FF03-178' resulted from the cross between the selections 'FL00-62' and the selection 'FL96-24' (unpatented selections). 'FF03-178' is a commercial variety intended for the hand harvest fresh market. The variety is medium vigorous, medium branched and leafy and produces a high yield of large fruit. 'FF03-178' has an estimated chilling requirement of 200 hours or less, but also produces high fruit yields in an evergreen production system with zero chill hours when the plants are not allowed to enter dormancy.

The new cultivar 'FF03-178' was selected in Lowell, Oreg. in 2003 from a seedling population resulted from a controlled cross between the parents, 'FL00-62' as female source and 'FL96-24' as male source.

The new variety 'FF03-178' has maintained its distinguishing characteristics throughout successive asexual propagations in Lowell, Oreg., as herein described, sweet and good flavor, firm berries, and vigorous plants that are very leafy and highly productive under primocane conditions.

The seedling family that produced 'FF03-178' was initially grown in 50 cell propagation trays and planted in Lowell, Oreg., USA in 2001. 'FF03-178' was selected in 2003 because it produced high quality fruit early in the season. After being selected in Oregon, 'FF03-178' was propagated by softwood cuttings and nine plant plots were established in Delano, Calif., USA and Oxnard, Calif., USA. The nine plant plots in California, USA were observed until they were removed in 2012. The performance of 'FF03-178' in California was considered good but not sufficiently good to justify commercialization. In 2012 and 2013, plants of 'FF03-178' were sent to trial sites in Colima, Mexico and Seville, Spain. In Mexico, 'FF03-178' possessed excellent fruit quality but the plant did not appear sufficiently vigorous to commercialize. In Seville, Spain however, 'FF03-178' did possess sufficient vigor to have good yields, and due to the extremely early ripening time of the 'FF03-178' in comparison to the varieties commercially available there, it was considered to have strong commercial potential. 'FF03-178' was selected for presenting an early concentrate production with high fruit quality under low chilling requirements. Fruit harvest can be medium-hard to pick. The fruit is fairly firm, sweet and present good flavor with medium-dried scar with good postharvest storage.

The new blueberry plant 'FF03-178' as it grows in Seville, Spain and elsewhere is distinguished by a moderately branched growth habit resulting in a rounded plant shape, low to moderate vigor, moderately spaced internodes, urceolate flowers with pink coloration before opening, very early flowering and fruiting, and firm, flavorful fruit with a moderately dark color and flattened shape. The following characteristics of the new cultivar have been repeatedly observed and can be used to distinguish 'FF03-178' as a unique *Vaccinium corymbosum* hybrid plant:

1. Very early fruit ripening (typically at the same time or before the very early ripening cultivar 'Snowchaser')
2. Excellent fruit flavor and very good fruit firmness
3. A very shallow calyx end depression on the ripe fruit
4. Highly evergreen leaves
5. Slightly oblate (flattened) fruit shape with weak to moderate bloom
6. Medium to high plant vigor The new variety 'FF03-178' has been stable in plant characteristic through multiple vegetative propagations. The parents 'FL00-62' and 'FL96-24' have not been evaluated side by side with 'FF03-178' in the same environment. However, in Florida, USA 'FL00-62' had fruit with a picking scar that was larger than that of FF03-178 in other locations. In Florida, USA 'FL00-62' also tended to have poor fruit coloration resulting in greenish portions of the ripe berry, whereas 'FF03-178' lacks this trait. The fruit of 'FL96-24' grown in Florida, USA were larger than typical fruit of 'FF03-178' grown elsewhere.

BRIEF DESCRIPTION OF THE DRAWINGS

The accompanying photographic illustration shows typical specimens in full color of the foliage and fruit of the new variety 'FF03-178' The colors are as nearly true as is reasonably possible in a color representation of this type.

Figure 1:
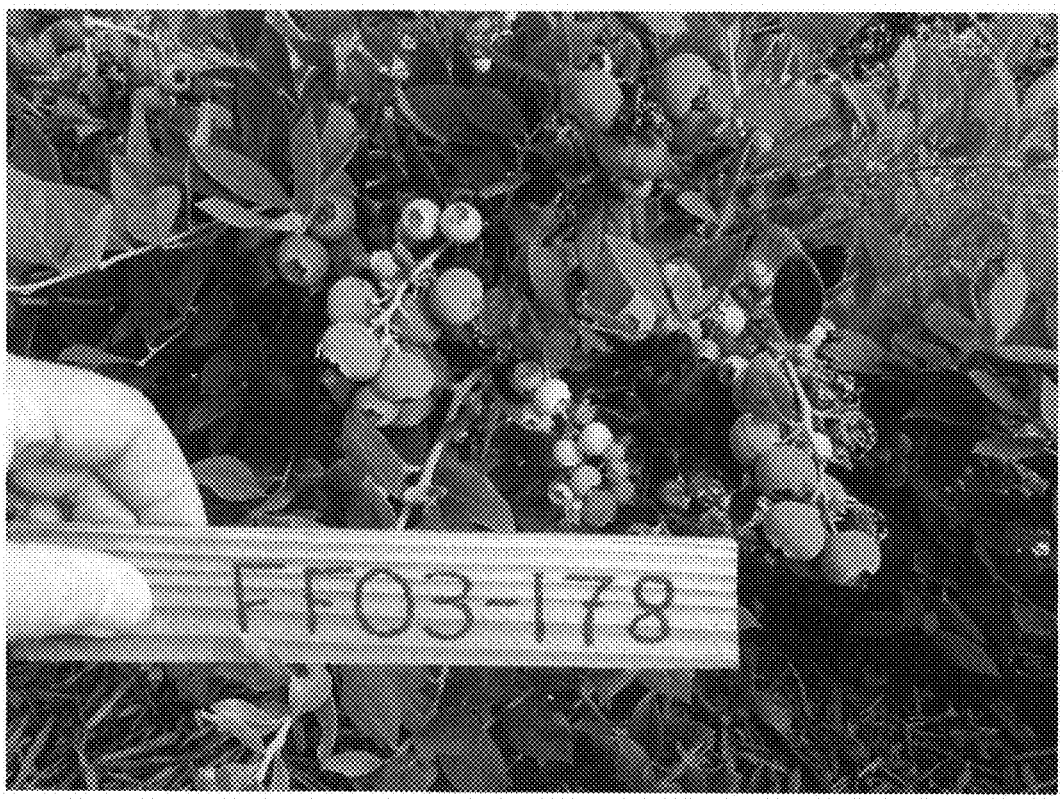
FIG. 1 is a photograph of the new variety 'FF03-178', demonstrating the plant's compact growth habit.
Figure 2:
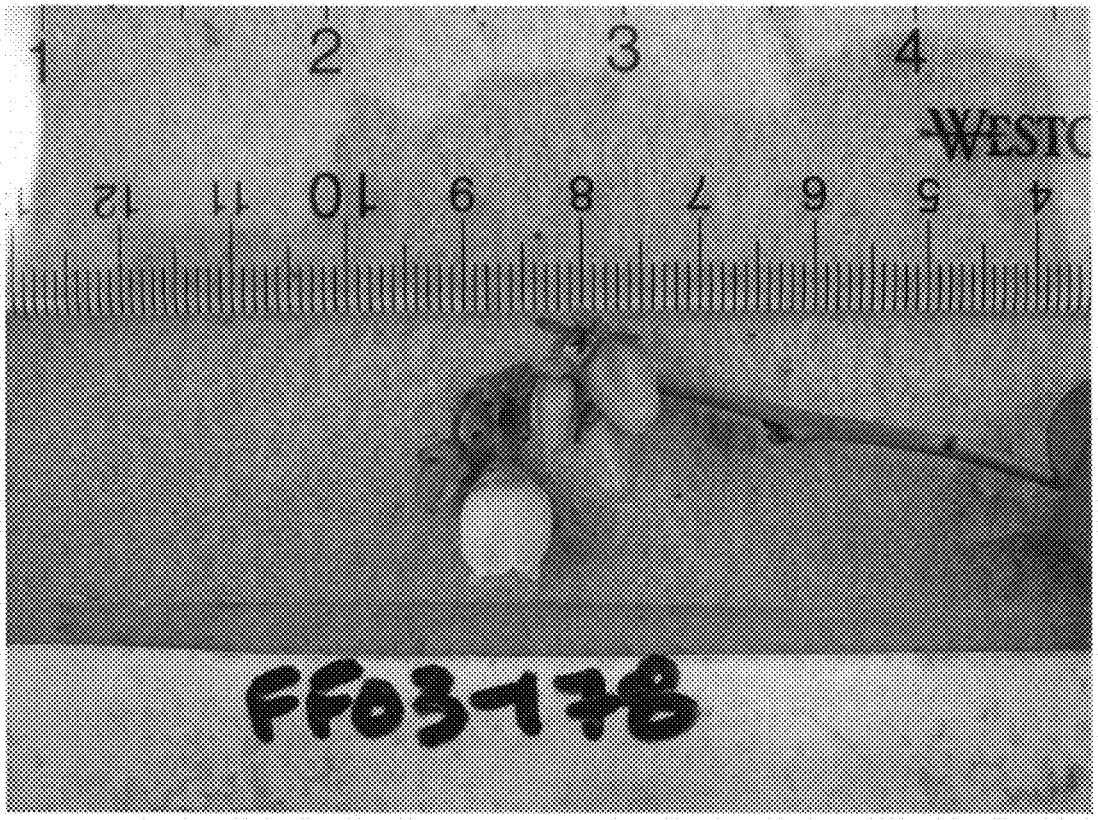
FIG. 2 is a photograph of the flowers of the new variety 'FF03-178'.
Figure 3:
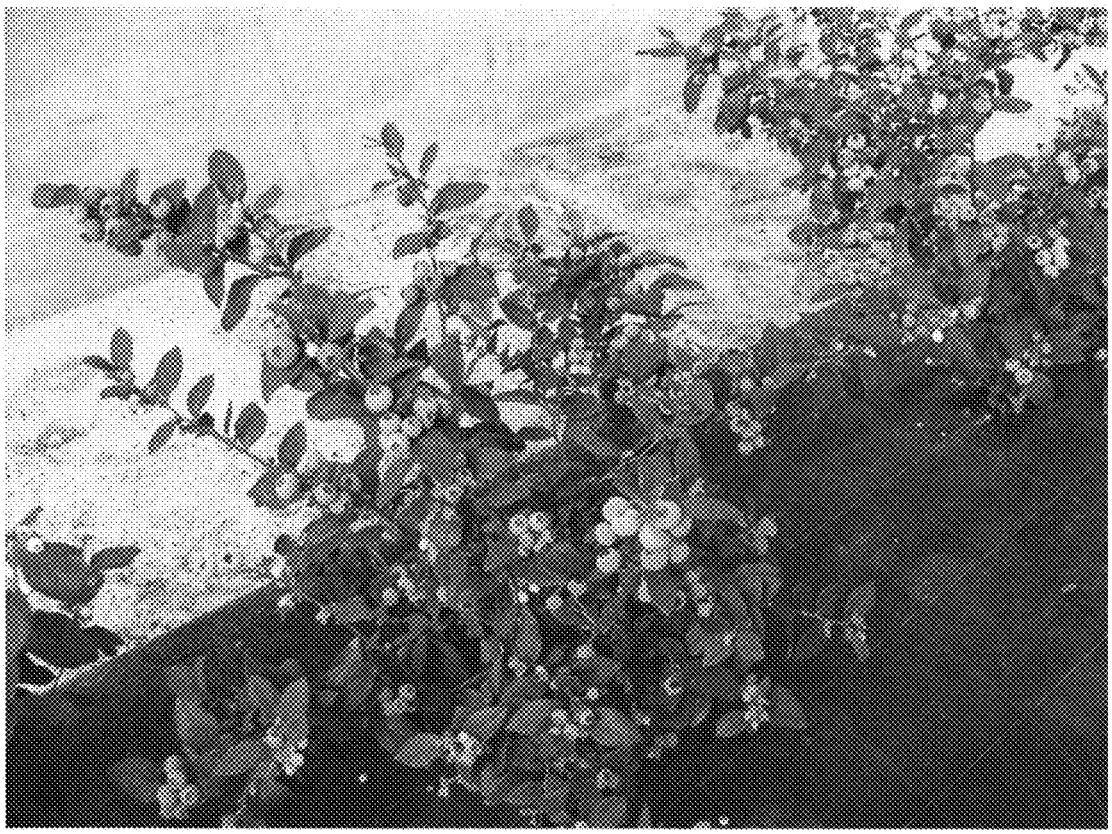
FIG. 3 is a photograph of the plant showing the fall foliage of the new variety 'FF03-178'.
Figure 4:
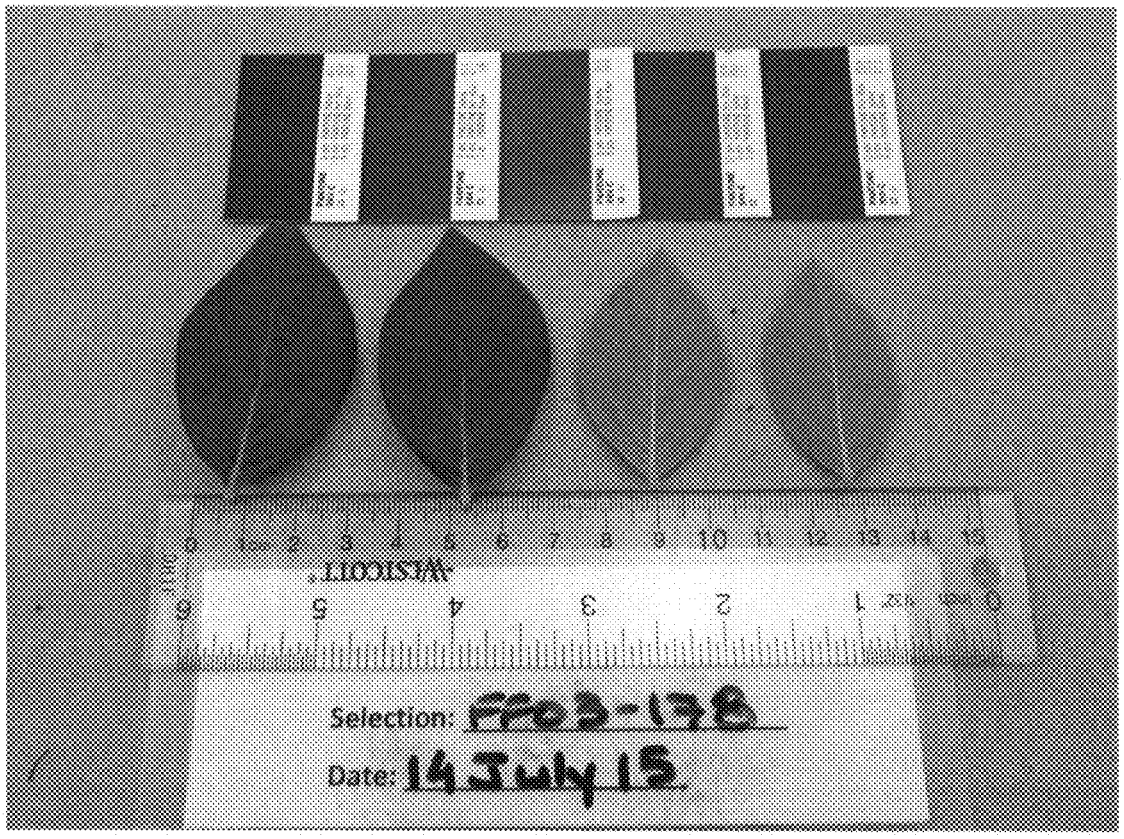
FIG. 4 is a photograph of the mature leaves adaxial and abaxial position of the new variety 'FF03-178'.
Figure 5:
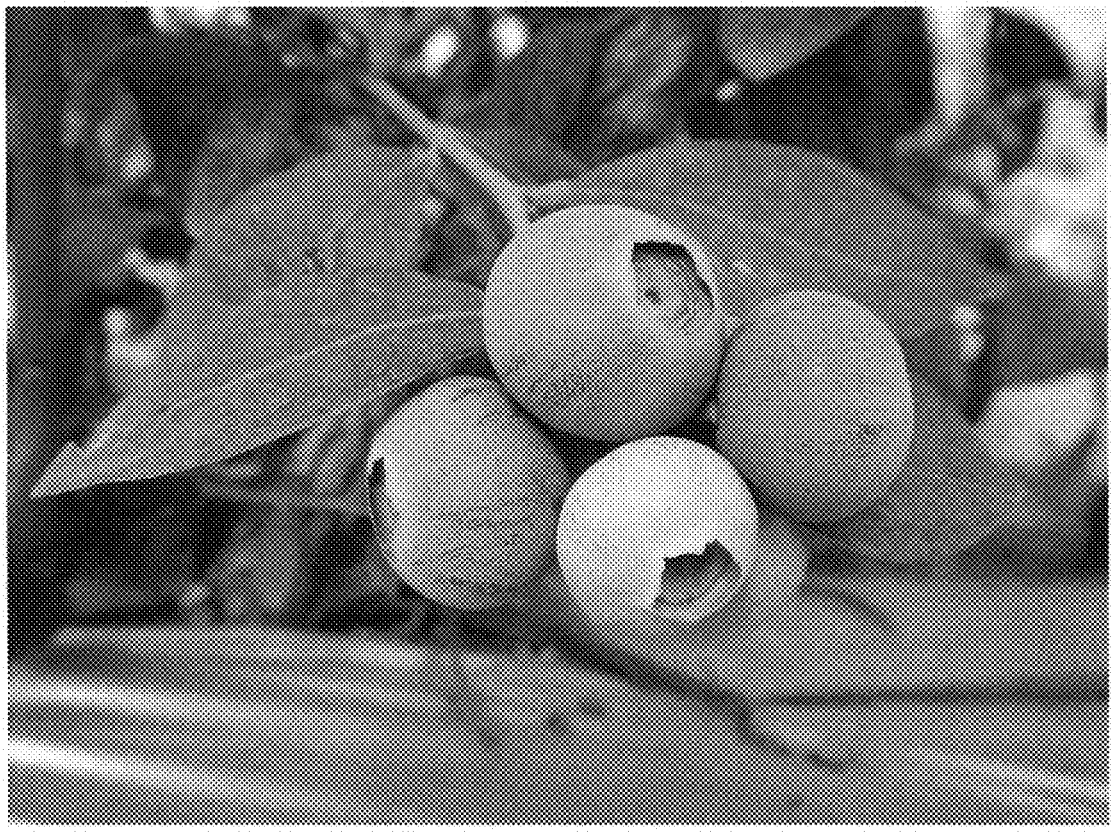
FIG. 5 is a photograph of the cluster on the variety 'FF03-178'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'FF03-178'. The data which define these characteristics were collected from asexual reproductions of the original selection. Dimensions, sizes, colors, and other characteristics are approximations and averages set forth as accurately as possible. The plant history was taken on plants approximately 3 years of age, and the descriptions relate to plants grown in the field in Tala, Jalisco Mexico. Descriptions of fruit characteristics were made on fruit grown in Tala, Jalisco Mexico. Color designations are from Pantone.

Classification:

*a. Family.*—Ericaceae.
*b. Genus.*—*Vaccinium.*
*c. Species.*—*corymbosum.*
*d. Common name.*—Highbush Blueberry.

Parentage:

*Female parent.*—'FL00-62' (unpatented).
*Male parent.*—'FL96-24' (unpatented).

Market class: Hand pick for fresh market.

PLANT

General:

*a. Parentage.*—'FL00-62'×'FL96-24'.
*b. Plant height.*—Average 0.6 m.
*c. Plant width.*—Average 0.7 m.
*d. Growth habit.*—Sprawling to round.
*e. Growth.*—Vigorous.
*f. Productivity.*—High.
*g. Cold hardiness.*—Approximately USDA hardiness zone 9-10.
*h. Cold tolerance.*—Medium.
*i. Chilling requirement.*—Approximately 200 hours or less.
*j. Tolerance to disease.*—To most common blueberry diseases. Not showing any special susceptibility to any pathogen.
*k. Leafing.*—Heavily leafy plant.
*l. Twigginess.*—High.

STEM

General:

*a. Suckering tendency.*—Low.
*b. Mature cane color.*—Pantone colors Carob Brown 18-1229, Gray Sand 13-1010, Mahogony 18-1425.
*c. Mature cane length.*—0.5 m.
*d. Mature cane width.*—3 cm.
*e. Bark texture.*—Rough.
*f. Fall color on new shoots.*—Carob Brown 18-1229.
*g. Surface texture of new wood.*—Smooth.
*h. Internode length on strong, new shoots.*—Average 12 mm.
*i. Fruiting wood.*—Average 16 cm in length.

FOLIAGE

General:

*a. Time of beginning of leaf bud burst.*—Evergreen under primocane production.
*b. Leaf color (top side).*—Burnt Olive 18-0521.
*c. Leaf color (under side).*—Tea 16-0213.
*d. Leaf arrangement.*—Alternate.
*e. Leaf shape.*—Obtuse.
*f. Leaf margins.*—Entire.
*g. Undulation of margin.*—Smooth.
*h. Leaf venation.*—Anastomosing.
*i. Leaf apices.*—Ovate.
*j. Leaf bases.*—Obtuse.
*k. Leaf length.*—Average 48 mm.

*l. Leaf width.*—Average 27 mm.
*m. Leaf length/width ratio.*—1.7.
*n. Leaf nectarines.*—Absent.
*o. Pubescence of upper side.*—Absent.
*p. Pubescence of lower side.*—Absent.
*q. Cross sectional profile.*—Revolute.
*r. Longitudinal profile.*—Entire.
*s. Attitude.*—Porrect.

Petioles:
*a. Length.*—Average 3.8 mm.
*b. Width.*—Average 2.2 mm.
*c. Color.*—Hay 12-0418.

FLOWERS

General:
*a. Time of beginning of flowering.*—November under primocane production.
*b. Time of* 50% *anthesis.*—Middle of December under primocane production.
*c. Flower shape.*—Urceolate.
*d. Flower bud density.*—Medium.
*e. Flower fragrance.*—Sweet.

Corolla:
*a. Color.*—Turtledove 12-5202.
*b. Length.*—Average 8.4 mm.
*c. Width.*—Average 9.8 mm.
*d. Aperture width.*—Average 4.4 mm.
*e. Anthocyanin coloration of corolla.*—Low.
*f. Corolla ridges.*—Distinct.
*g. Protrusion of stigma.*—Nule.

Inflorescence:
*a. Length.*—Average 23 mm.
*b. Diameter.*—Average 20 mm.
*c. Length of peduncle.*—Average 20 mm.
*d. Surface texture of peduncle.*—Smooth.
*e. Color of peduncle.*—Green Olive 17-0535.
*f. Length of pedicel.*—Average 5.6 mm.
*g. Surface texture of pedicel.*—Smooth.
*h. Color of pedicel.*—Leaf Green 15-0332.
*i. Number of flowers per cluster.*—Average 4.
*j. Flower cluster density.*—Lose.

Calyx (with sepals):
*a. Diameter.*—Average 7.2 mm.
*b. Color* (*sepals*).—Herbal Garden 15-0336.

Stamen:
*a. Length.*—Average 5.8 mm.
*b. Number per flower.*—Average 10.
*c. Filament color.*—White Jade 12-0315.
*d. Style: length.*—Average 5.1 mm.
*e. Color.*—Golden Ochre 16-1346.

Pistil:
*a. Length.*—Average 5.1 mm.
*b. Ovary color* (*exterior*).—Grasshopper 18-0332.

Anther:
*a. Length.*—Average 4.2 mm.
*b. Number.*—Average 10.
*c. Color.*—Golden Ochre 16-1346.

Pollen:
*a. Abundance.*—High.
*b. Color.*—Pastel Pergament 11-0603.
*c. Self-compatibility.*—Low, but it can set parthenocarpic fruit.

FRUIT

General:
*a. Time of fruit ripening.*—From February 15 to April 30 under primocane production.
*b. Time of* 50% *maturity.*—Average March 20$^{th}$ under primocane production.
*c. Fruit development period.*—Average 56 days.
*d. Cluster density.*—Average 4_ berries per cluster.
*e. Unripe fruit color.*—Asparagus Green 12-0311.
*f. Ripe berry color.*—Lilac Gray 14-3903.
*g. Berry surface wax abundance.*—Medium.
*h. Berry flesh color.*—White Jade 12-031.
*i. Berry weight.*—Average 2.4 g under cross pollination conditions.
*j. Berry height from calyx to scar.*—Average 13.3 mm.
*k. Berry diameter.*—Average 18.4 mm.
*l. Berry shape.*—Oblate.
*m. Fruit stem scar.*—Small and dry.
*n. Sweetness when ripe.*—Medium.
*o. Firmness when ripe.*—Medium.
*p. Acidity when ripe.*—Medium.
*q. Storage quality.*—Good.
*r. Suitability for mechanical harvesting.*—Low.
*s. Self-fruitfulness.*—Yes.
*t. Uses.*—Fresh.

SEED

General:
*a. Seed abundance in fruit.*—38 in cross pollination.
*b. Seed color.*—Nugget 16-1148.
*c. Seed dry weight.*—40 mg per 100 seeds.
*d. Seed length.*—Average 1.72 mm.

COMPARISON BETWEEN PARENTAL AND COMMERCIAL CULTIVARS

The new variety 'FF03-178' have not been evaluated under the same environment as the parents, as contrasting characteristics, 'FL00-62' had fruit with a picking scar stronger than in 'FF03-178' in other locations, also it usually presents a poor fruit coloration of ripe berries, but it has not been observed in 'FF03-178'. The fruit of 'FL96-24' was observed as bigger than the typical fruit of 'FF03-178' evaluated in different locations.

The invention claimed is:

1. A new and distinct variety of blueberry plant named 'FF03-178' substantially as illustrated and described herein.

* * * * *